United States Patent [19]

Malkowska et al.

[11] Patent Number: 5,071,646
[45] Date of Patent: Dec. 10, 1991

[54] PHARMACEUTICAL ION EXCHANGE RESIN COMPOSITION

[75] Inventors: Sandra T. A. Malkowska, Ely; Ian R. Buxton, Histon; Derek A. Prater, Milton; Alison A. Norman, Somersham, all of Great Britain

[73] Assignee: Euroceltique, S.A., Luxembourg

[21] Appl. No.: 434,416

[22] Filed: Nov. 9, 1989

[30] Foreign Application Priority Data

Nov. 11, 1988 [GB] United Kingdom ............... 8826407
Dec. 7, 1988 [GB] United Kingdom ............... 8828592

[51] Int. Cl.$^5$ .................. A61K 9/16; A61K 47/00; A61J 3/02; C08J 3/12
[52] U.S. Cl. ............................ 424/497; 424/458; 424/459; 424/460; 424/461; 424/462; 424/501; 424/500; 424/491; 424/494; 424/495; 424/497; 424/498; 424/457; 424/78.1; 424/78.12; 514/951; 514/952; 523/122

[58] Field of Search ............ 424/79, 452, 457, 501; 514/952, 963

[56] References Cited

U.S. PATENT DOCUMENTS

| 4,221,778 | 9/1980 | Raghunathan | 424/483 |
| 4,369,175 | 1/1983 | Khanna | 424/79 |
| 4,404,346 | 9/1983 | Pirotta et al. | 424/79 |
| 4,847,362 | 7/1989 | Mathews et al. | 514/822 |

Primary Examiner—Thurman K. Page
Assistant Examiner—Edward J. Webman
Attorney, Agent, or Firm—Steinberg & Raskin

[57] ABSTRACT

An ion exchange resin composition which is readily dispersible in water is provided. This resin composition comprises a granulated ion exchange resin, a pharmacologically active ingredient bound thereto with a sugar or sugar alcohol, and a sufficient amount of water, alcohol or aqueous alcohol to facilitate granulation. The invention further comprises a method for the preparation of such ion exchange resin composition.

10 Claims, No Drawings

PHARMACEUTICAL ION EXCHANGE RESIN COMPOSITION

BACKGROUND OF THE INVENTION

Ion exchange resin compositions containing pharmacologically active ingredients are known. However, one of the major drawbacks of the known compositions is that the same are not sufficiently dispersible in water. The lack of dispersibility in water reduces the time required for the pharmacological agent to act.

SUMMARY OF THE INVENTION

It is accordingly a primary object of the present invention to provide pharmaceutical ion exchange resins with a high degree of dispersibility in water.

It is yet a further object of the present invention to provide a method of producing the water dispersible pharmaceutical ion exchange resins.

Other objects and advantages of the present invention will be apparent from a further reading of the specification and of the appended claims.

With the above and other objects in view, the present invention mainly comprises a pharmaceutical ion exchange resin composition which is readily dispersible in water, said composition comprising a granulated ion exchange resin having a pharmacologically active ingredient bound thereto, by means of a sugar or sugar alcohol in the presence of a sufficient amount of water, alcohol or aqueous alcohol to facilitate the granulation.

The phrase "readily dispersible in water" in accordance with the present invention, means that the composition must disperse, with stirring in twenty times its own weight of water within ten seconds.

The present invention is applicable to any acidic or basic drug, which may be bound to the ion exchange resin. Preferably, however, active ingredients having a biological half life of eight hours or less are used.

Among the suitable types of pharmacological active agents that can be used in accordance with the present invention are the following:
i) Narcotic analgesics, such as codeine, dihydrocodein, hydromorphone, morphine, pentazocine and propoxyphene,
ii) Sympathomimetics, such as norephedrine and pseudoephedrein,
iii) Antitussives, such as dextromethorphan,
iv) Analgesics, such as aspirin,
v) Antiemetics, such as metoclopramide,
vi) Anticholinergics, such as atropine, ipratropium bromide and scopolamine,
vii) Muscle relaxants, such as cyclobenzaprine and papaverine,
viii) Bronchodilators, such as salbutamol, terbutaline and theophylline,
ix) Antibiotics, such as amoxycillin, ampicillin, azlocillin, bacampicillin, cefamandole, cefonicid, cefotaxime, cefotetan, cefoxitin, ceftriaxone, mezlocillin and piperacillin,
x) Antidepressants, such as bupropion, nomifensine, and nortripyline,
xi) Antiasthmatics, such as cromolyn,
xii) Antineoplastics, such as tamoxifen,
xiii) Antiepileptics, such as valproic acid and phenytoin,
xiv) Cardiovascular agents, such as propranolol.

Any of the above may be used in the form of their acid addition salts, or, if appropriate, alkali or alkaline earth metal salts.

A wide variety of resins may be used for the purposes of the present invention. In the case of basic drugs, any pharmacologically compatible cationic resin may be used. In the case of acidic drugs, any pharmacologically compatible anionic resin may be used.

Suitable ion exchange resins generally have acrylic, methacrylic, phenol-formaldehyde or dextran matrices. However, a preferred cationic ion exchange resin is a gel styrene-divinyl benzene sulphonic acid resin, such as Amberlite IR 120 (Trademark) Amberlite XE 69 (Trademark) and Dowex 50W (Trademark), while a preferred anionic ion exchange resin is a gel styrene-divinyl benzene quaternary ammonium resin, such as Dowex SBR (Trademark) and Dowex SAR (Trademark).

The particle size and, if applicable, the degree of cross linking of the resin is determined by, among other factors, the drug employed and the rate of drug release required. Preferably, however, the resin has a particle size of from 0.045 to 1 mm, especially from 0.045 to 0.5 mm. If applicable, the preferred degree of cross-linking is from 2% to 16% particularly from 8% to 12%.

The amount of drug bound to the resin is also determined by the choice of drug, as well as by the resin employed. Preferably the weight ratio of bound drug to resin is from 1:3 to 2:1 particularly from 2:3 to 3:2.

Absorption of the drug onto the ion exchange resin particles is a well known technique as shown in British Patent Nos. 824,337 and 1,218,102 and U.S. Pat. No. 2,990,332, and demonstrated in the examples below. In general, the drug is mixed with an aqueous suspension of the resin and the complex is then dried. Adsorption of the drug onto the resin is detected by an assay of the suspending fluid.

Preferably the sugar or the sugar alcohol has a molecular weight of from 90 to 550, especially from 150 to 370. Suitable sugars and sugar alcohols are sucrose, dextrose, maltose, fructose, lactose, mannitol, sorbitol or most preferably xylitol. The sugar or sugar alcohol is preferably finely divided, all of the sugar or sugar alcohol preferably having particle sizes of 600 microns or less (30 mesh sieve). In a particularly preferred embodiment of the present invention, at least 90% (by weight) of the sugar/sugar alcohol will have particle sizes of 250 microns or less (60 mesh sieve).

The concentration of the sugar/sugar alcohol in the composition of the present invention must be high enough to allow the composition to disperse readily in water. This means that there must be enough sugar/sugar alcohol present to allow the composition to disperse (within 10 seconds) when added with stirring to 20 times its weight of water. Generally, the composition will contain from 25% to 99%, preferably from 70% to 95% (by weight) of the sugar/sugar alcohol.

The drug-resin complex and the sugar/sugar alcohol are granulated in the presence of sufficient water, aqueous alcohol or alcohol to facilitate granulation. The most suitable alcohols are $C_1$-$C_4$ aliphatic alcohols, especially those having a boiling point, at 760 mm Hg of 100° C. or less. Preferred alcohols are ethanol and isopropanol.

Preferably, the amount of granulating medium (water, alcohol or aqueous alcohol) employed is from 10 to 20%, especially from 2 to 7% by weight of the weight of the complex/sugar, sugar alcohols mix. In a particularly preferred embodiment of the present process the mixture is granulated until the particle size of the sugar/sugar alcohol matches the resin particle size. In the present specification, "matches" means that at least 80% (by weight) of the sugar/sugar alcohol has a particle size between 0.5 and 1.5 times the mean particle size of the drug-resin complex. Once the drug-resin complex and the sugar/sugar alcohol have been granulated, the granules formed are then dried, preferably until their water content is below 3% (by weight), when measured by the Karl Fischer method of moisture analysis.

Optionally, the drug-resin complex or the granules may be film coated with a material that permits release of the drug from the composition at the controlled rate.

The film coat will generally include a water insoluble material such as:

(a) a wax, either alone or in admixture with a fatty alcohol
(b) shellac or zein,
(c) a water insoluble cellulose derivative, especially ethyl cellulose
(d) a polymethacrylate, especially Eudragit (trademark).

Preferably, the film coat comprises a mixture of the water insoluble material and a water soluble material. The ratio of water insoluble to water soluble material is determined by among other factors, the release rate required and the solubility characteristics of the materials selected.

The water soluble material may be, for example, triacetin, propylene glycol, polyethylene glycol, polyvinylpyrrolidone or, which is preferred, a water soluble cellulose, such as hydroxypropyl cellulose, or especially, hydroxypropylmethyl cellulose.

Suitable combinations of water insoluble and water soluble materials for the film coat include shellac and polyvinylpyrrolidone or, preferable ethyl cellulose and hydroxypropylmethyl cellulose.

Once the above processing is complete, the composition may then be presented in a suitable dosage form, such as a capsule or sachet. This is done simply by filling the capsule or sachet with the finished composition.

DESCRIPTION OF PREFERRED EMBODIMENTS

The following examples are given to further illustrate the present invention. The scope of the invention is not, however, meant to be limited to the specific details of the examples.

EXAMPLE 1

Morphine sulphate (pentahydrate, 300 gm) was added to purified water (EP, 110 gm) and mixed until all of the powder was evenly wetted. With continuous mixing a cationic exchange resin, Dowex W50×8-200, (Trademark) hydrous approx 50% (by weight) water, 60 gm) was added to the morphine suspension. The stirring was continued for 24 hours at a rate that kept the resin suspended. The resin was then washed with purified water and dried in a fluid bed dryer.

Xylitol, (500 gm 90% (by weight) having a particle size less than 200 μm) was mixed with the morphine-resin complex (50 gm) and xanthan gum (200 gm) in a granulator. With continuous mixing, purified water was added to the mixture until evenly wetted light granules were formed.

Generally the amount of water added was 2.0–5.0% (by weight) of the xylitol/complex/xanthan gum weight. The moist granules were then dried in a fluid bed dryer until the water content was below about 3.0% (by weight), Karl Fischer method).

Each unit dose of this composition had the following formulation,

|  | mg/unit dose |
|---|---|
| Morphine Sulphate (absorbed on the resin as morphine base) | 20 |
| Dowex W50x8-200 (Trademark) | 20 |
| Xylitol | 500 |
| Xanthan Gum | 20 |

EXAMPLE 2 the process of Example 1 was repeated to form a composition having the following formulation:

|  | mg/unit dose |
|---|---|
| Metoclopramide Hydrochloride (absorbed on the resin as metoclopramide base | 15 |
| Dowex W50x8-200 (Trademark) | 15 |
| Xylitol | 500 |
| Xanthan Gum | 20 |

EXAMPLE 3

The process of Example 1 was repeated to form a composition having the following formation:

|  | mg/unit dose |
|---|---|
| Hydromorphone Hydrochloride (absorbed on the resin as hydromorphone base) | 4 |
| Dowex W50x16-100 (Trademark) | 12 |
| Xylitol | 500 |
| Xanthan Gum | 20 |

EXAMPLE 4

The process of Example 1 was repeated to form a composition having the following formulation:

|  | mg/unit dose |
|---|---|
| Theophylline Sodium (absorbed on the resin as theophylline base) | 100 |
| Dowex 2x8-200 (Trademark) | 200 |
| Xylitol | 870 |
| Xanthan Gum | 45 |
| Polyoxy 40-stearate (trademark) | 5 |

COMPARATIVE EXAMPLE

The process of Example 1 was repeated except that the xylitol/morphine-resin complex/xanthan gum was dry mixed to form a powder, rather than wet granulated.

DISPERSIBILITY OF RESIN COMPOSITIONS IN WATER

Unit doses of the granular and powder products, produced according to Example 1 and the Comparative Example, respectively, were added to 100ml of water with continuous mixing.

The granular product immediately (within 10 seconds) formed an aqueous suspension of the resin. By contrast, the powder product formed a wetted mass that took a number of minutes to disperse in the aqueous medium (and thereby form a resin suspension).

Furthermore, while the granulated product gives a homogeneous product in which the drug substance is dispersed uniformly throughout the composition, the dry mixed powder was non-homogenous, the drug substance being non-uniformly distributed throughout the composition.

While the invention has been described in particular with respect to the above examples, it is apparent that variations and modifications of the invention can be made without departing from the spirit and scope thereof.

What is claimed is:

1. Method of producing a pharmaceutical ion exchange resin composition that is readily dispersible in water, said method comprising granulating a pharmaceutically compatible ion exchange resin, having a pharmacologically active ingredient bound thereto, with a sugar or sugar alcohol in an amount of 25-99% by weight of the composition in the presence of a sufficient amount of water, alcohol or aqueous alcohol to facilitate granulation.

2. Method according to claim 1 wherein said sugar of sugar alcohol is sucrose, dextrose, maltose, fructose, lactose, mannitol, sorbitol of xylitol.

3. Method according to claim 1 wherein said sugar of sugar alcohol is xylitol.

4. Method according to claim 1 wherein said sugar of sugar alcohol has a particle size of 600 microns or less.

5. Method according to claim 1 wherein at least 90% by weight of said sugar of sugar alcohol has a particle size of 250 microns or less.

6. Method according to claim 1 wherein the amount of sugar or sugar alcohol is between 70-95% by weight.

7. Method according to claim 1 the amount of water, alcohol or aqueous alcohol utilized is in an amount of 1-20% by weight of the combined weight of said pharmacologically active agent, said resin and said sugar or sugar alcohol.

8. Method according to claim 1 wherein the granulation is continued until the particle size of the ion exchange resin matches the particle size of the sugar or sugar alcohol.

9. Method according to claim 1 wherein after granulation the granules are dried until the water content thereof is below 3% by weight.

10. Method according to claim 1, wherein the amount of water, aqueous alcohol or alcohol utilized is in an amount of 2%-7% by weight of the combined weight of the pharmacologically active ingredient, resin and the sugar or sugar alcohol.

* * * * *